(12) United States Patent
Umebayashi et al.

(10) Patent No.: US 7,972,319 B2
(45) Date of Patent: Jul. 5, 2011

(54) WEARING ARTICLE AND METHOD OF MANUFACTURING THE SAME

(75) Inventors: Toyoshi Umebayashi, Settsu (JP); Shuhei Kurata, Settsu (JP)

(73) Assignee: Zuiko Corporation (JP)

( * ) Notice: Subject to any disclaimer, the term of this patent is extended or adjusted under 35 U.S.C. 154(b) by 715 days.

(21) Appl. No.: 11/919,019

(22) PCT Filed: Apr. 27, 2006

(86) PCT No.: PCT/JP2006/308892
§ 371 (c)(1),
(2), (4) Date: Oct. 22, 2007

(87) PCT Pub. No.: WO2006/118214
PCT Pub. Date: Nov. 9, 2006

(65) Prior Publication Data
US 2009/0312739 A1 Dec. 17, 2009

(30) Foreign Application Priority Data

Apr. 28, 2005 (JP) ................................ 2005-132894
Apr. 28, 2005 (JP) ................................ 2005-132895

(51) Int. Cl.
*A61F 13/15* (2006.01)

(52) U.S. Cl. .............. 604/385.29; 604/358; 604/385.25; 156/150; 156/269

(58) Field of Classification Search ............. 604/385.29, 604/385.25; 156/150, 269
See application file for complete search history.

(56) References Cited

U.S. PATENT DOCUMENTS

| 4,612,674 | A | * | 9/1986 | Hashimoto | 2/406 |
| 5,110,386 | A | * | 5/1992 | Ochi et al. | 156/204 |
| 5,985,018 | A | * | 11/1999 | Link et al. | 106/287.25 |
| 6,514,233 | B1 | * | 2/2003 | Glaug | 604/385.25 |
| 6,827,804 | B2 | * | 12/2004 | Otsubo et al. | 156/161 |
| 6,979,380 | B2 | * | 12/2005 | Thorson et al. | 156/259 |

(Continued)

FOREIGN PATENT DOCUMENTS

EP   1 285 644 A2   2/2003

(Continued)

OTHER PUBLICATIONS

PAJ (Patent Abstracts of Japan): Translation of JP 2000-093462 (Komatsu et al) 16 pp.*

*Primary Examiner* — Melanie J Hand
*Assistant Examiner* — Ginger T Chapman
(74) *Attorney, Agent, or Firm* — Gerald E. Hespos; Michael J. Porco

(57) ABSTRACT

A wearing article capable of suppressing the occurrence of a loss of materials and an increase of the cost of facilities and a method of manufacturing the same are provided. A wearing article includes a waist portion (3) formed in a ring shape capable of continuously surrounding the waist of the wearer and using one of openings as a waist opening (9), and a crotch portion (4) joined to the waist portion (3) across an opening on the opposite side to the waist opening (9) so that the crotch portion (4) and the waist portion (3) define a pair of leg openings (10) for the wearer to put through his legs individually. Shirring is formed in the crotch portion (4) so as to shorten the distance between the mutually opposing inner surfaces of the waist portion (3) connected to each other by the crotch portion (4).

6 Claims, 10 Drawing Sheets

U.S. PATENT DOCUMENTS

| | | | |
|---|---|---|---|
| 6,984,279 B2 * | 1/2006 | Mortell et al. | 156/211 |
| 7,198,688 B2 | 4/2007 | Mortell et al. | |
| 7,220,335 B2 * | 5/2007 | Van Gompel et al. | 156/259 |
| 7,393,429 B2 * | 7/2008 | Tachibana | 156/256 |
| 7,407,557 B2 | 8/2008 | Wada et al. | |
| 2002/0046802 A1 * | 4/2002 | Tachibana et al. | 156/209 |
| 2002/0103468 A1 * | 8/2002 | Nakakado et al. | 604/358 |
| 2003/0040732 A1 | 2/2003 | Ishikawa et al. | |
| 2004/0107481 A1 * | 6/2004 | Mortell et al. | 2/400 |
| 2004/0112508 A1 * | 6/2004 | Umebayashi et al. | 156/160 |
| 2005/0241747 A1 * | 11/2005 | Allen | 156/204 |
| 2006/0161131 A1 | 7/2006 | Kurata et al. | |
| 2006/0174400 A1 | 8/2006 | Kurata | |
| 2010/0262110 A1 * | 10/2010 | Lakso | 604/385.3 |

FOREIGN PATENT DOCUMENTS

| | | |
|---|---|---|
| EP | 1 574 193 A1 | 9/2005 |
| EP | 1 600 067 A1 | 11/2005 |
| JP | 2000-93462 | 4/2000 |
| WO | 2004/037145 A1 | 5/2004 |
| WO | WO 2004/052131 | 6/2004 |
| WO | 2004/054490 A1 | 7/2004 |
| WO | 2004/060252 A1 | 7/2004 |
| WO | 2004/062398 A1 | 7/2004 |

* cited by examiner

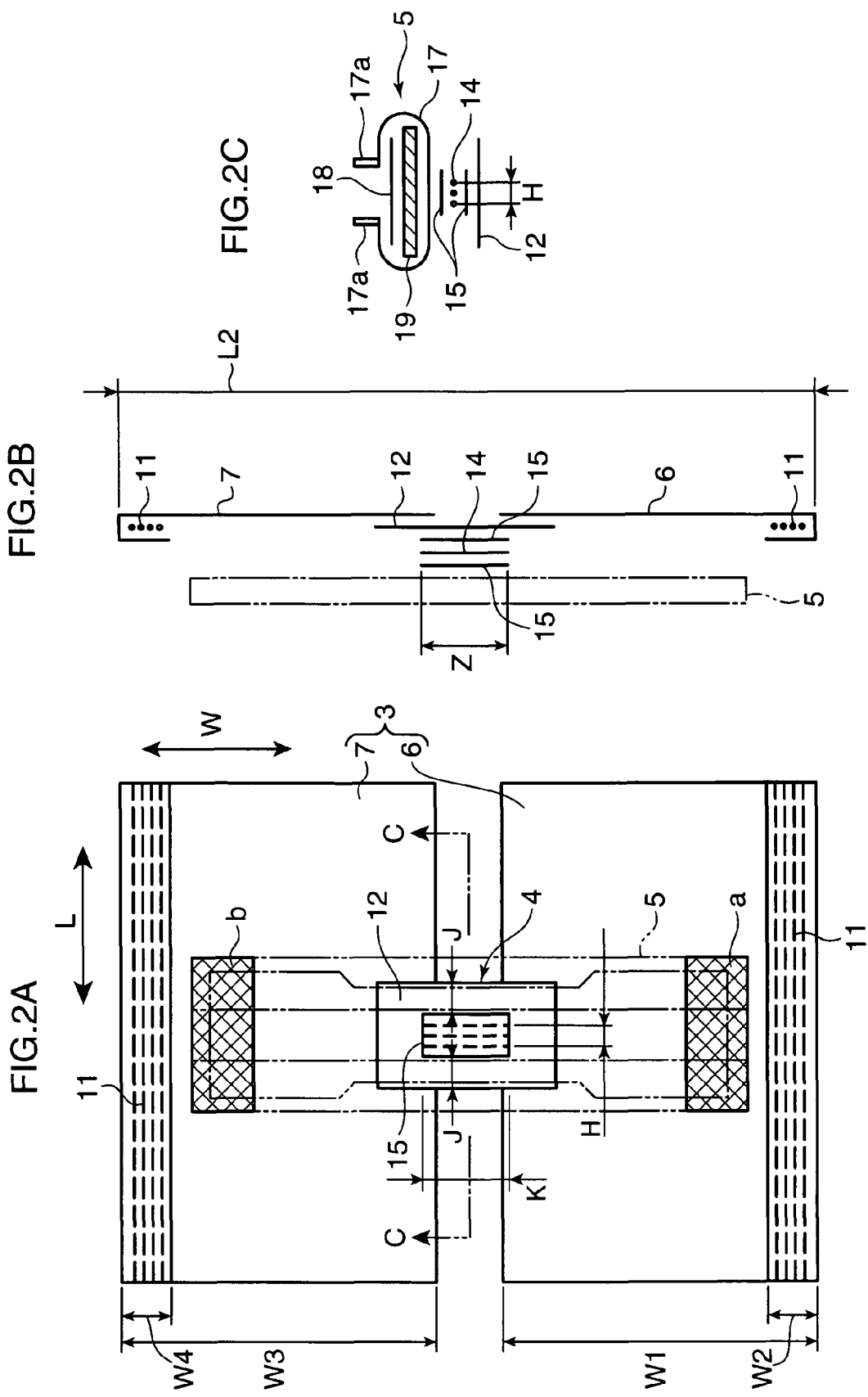

WEARING ARTICLE AND METHOD OF MANUFACTURING THE SAME

BACKGROUND OF THE INVENTION

1. Field of the Invention

The present invention relates to a wearing article and a method of manufacturing the same.

2. Description of the Related Art

For instance, boxer shorts known as the wearing article are manufactured by the manufacturing method disclosed in Patent Document 1.

The manufacturing method of Patent Document 1 adopts the step of transporting a strip-shaped web along the longitudinal direction thereof while making leg openings penetrating through the web in the thickness direction, and then folding the web in the width direction.

However, because leg openings are made in the web, the manufacturing method of Patent document 1 has problems that not only pieces cut away from the web to be thrown away result in the occurrence of a loss of materials, but also the need for a special apparatus for cutting out the web increases the cost of facilities.

The invention was devised in view of the problems discussed above and therefore has an object to provide a wearing article capable of suppressing the occurrence of a loss of materials and an increase in the cost of facilities and a method of manufacturing the same.

Patent Document 1: WO 2004/052131

SUMMARY OF THE INVENTION

In order to solve the problems above, the invention provides a wearing article, characterized by including a waist portion formed in a ring shape capable of continuously surrounding a waist of a wearer and using one of openings as a waist opening, and a crotch portion joined to the waist portion across an opening on an opposite side to the waist opening so that the crotch portion and the waist portion define a pair of leg openings for the wearer to put through his legs individually, wherein the crotch portion is formed with shirring in which the crotch portion is let to shrink in a direction in which mutually opposing inner surfaces of the waist portion come closer to each other.

According to the invention, because the opening in the waist portion is divided into two parts by the crotch portion and these parts are used as leg openings, it is possible to form the respective leg openings without the work to cut out the waist portion.

Hence, according to the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, the fastening occurs in the crotch portion by the shirring (corrugated shape formed by gathering a sheet material in folds, such as gathers, pleats, and creases) formed in the crotch portion. The crotch portion is therefore pulled upward (in a direction toward the waist opening from the leg openings) and forms a gusset when put on the wearer, and the wearing article takes on the shape of a trunks type. It is thus possible to achieve satisfactory wearing comfort and enhance the appearance when put on the wearer.

Also, the invention provides a method of manufacturing a wearing article having a front portion disposed on an abdomen of a wearer and a back portion disposed on a back of the wearer, characterized by including: a front outer web transporting step of transporting a strip-shaped front outer web used to form the front portion in such a manner that a longitudinal direction thereof aligns with a pre-set flowing direction; a back outer web transporting step of transporting a strip-shaped back outer web used to form the back portion in parallel with the front outer web with a specific interval from the front outer web; a joining step of disposing a crotch outer sheet so as to bridge between the both outer webs and joining the crotch outer sheet onto the both outer webs; a shirring forming step of forming shirring in the crotch outer sheet along a direction crossing the flowing direction; a folding step of placing the front outer web and the back outer web one on top of the other by folding the crotch outer sheet; and a cutting step of joining the front outer web and the back outer web along a width direction of the both outer webs at positions on both sides of the crotch outer sheet and cutting the both outer webs for every wearing article.

According to the invention, it is possible to manufacture a wearing article in which the both outer webs are joined in a ring shape and one of the openings is divided into two parts by the crotch outer sheet by providing the crotch outer sheet across a space between the front outer web and the back outer web and by joining the both outer webs placed one on top of the other by folding the crotch outer sheet on the both sides of the crotch outer sheet.

More specifically, according to the manufacturing method described above, because clearances corresponding to the leg openings can be formed on the both sides of the crotch outer sheet by joining the crotch outer sheet to the strip-shaped front outer web and the strip-shaped back outer web across a space therebetween, it is possible to form the leg openings without performing the work to cut out the both outer webs.

Hence, according to the manufacturing method of a wearing article of the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, because the shirring is formed in the crotch outer sheet along the direction crossing the flowing direction, the fastening occurs in the crotch portion in the completed wearing article by the shirring formed in the crotch portion (crotch outer web). The crotch portion is therefore pulled upward and forms a gusset when put on the wearer, and the wearing article takes on the shape of a trunks type. It is thus possible to achieve satisfactory wearing comfort and enhance the appearance when put on the wearer.

In the invention, the phrase, "cut the both outer webs for every wearing article", means to cut the outer webs for every region including a pair of joined parts formed on the both sides of the crotch outer sheet.

Also, the invention provides a method of manufacturing a wearing article having a front portion disposed on an abdomen of a wearer and a back portion disposed on a back of the wearer, characterized by including: a front outer web transporting step of transporting a strip-shaped front outer web used to form the front portion in such a manner that a longitudinal direction thereof aligns with a pre-set flowing direction; a back outer web transporting step of transporting a strip-shaped back outer web used to form the back portion in parallel with the front outer web with a specific interval from the front outer web; an outer sheet joining step of disposing a crotch outer sheet so as to bridge between the both outer webs and joining the crotch outer sheet onto the both outer webs; an attaching step of attaching a first crotch elastic member in a stretched state to the crotch outer sheet in a direction crossing the flowing direction; a maintaining step of maintaining the first crotch elastic member in the stretched state; a folding step of placing the front outer web and the back outer web one on top of the other by folding the crotch outer sheet; and a cutting step of joining the front outer web and the back outer web along a width direction of the both outer webs at positions on both sides of the crotch outer sheet and cutting the both outer webs for every wearing article.

According to the invention, it is possible to manufacture a wearing article in which the both outer webs are joined in a ring shape and one of the openings is divided into two parts by the crotch outer sheet by providing the crotch outer sheet across a space between the front outer web and the back outer web and by joining the both outer webs placed one on top of the other by folding the crotch outer sheet on the both sides of the crotch outer sheet.

More specifically, according to the manufacturing method described above, because clearances corresponding to the leg openings can be formed on the both sides of the crotch outer sheet by joining the crotch outer sheet to the strip-shaped front outer web and the strip-shaped back outer web across a space therebetween, it is possible to form the leg openings without performing the work to cut out the both outer webs.

Hence, according to the manufacturing method of a wearing article of the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, because the first crotch elastic member in a stretched state can be attached to a region that will be made into the crotch portion when the wearing article is completed, fastening occurs in the crotch portion in the completed wearing article due to a shrinkage force of the first crotch elastic member. The crotch portion is therefore pulled upward and forms a gusset when put on the wearer, and the wearing article takes on the shape of a trunks type. It is thus possible to achieve satisfactory wearing comfort and enhance the appearance when put on the wearer.

BRIEF DESCRIPTION OF THE DRAWINGS

FIG. 2 is a development view of the disposable pants of FIG. 1A, and FIG. 2A is a plan view, FIG. 2B is a side view of FIG. 2A, and FIG. 2C is a cross section taken on line C-C of FIG. 2A.

DETAILED DESCRIPTION OF THE PREFERRED EMBODIMENTS

Hereinafter, preferred embodiments of the invention will be described with reference to the drawings.

Figure 1A:
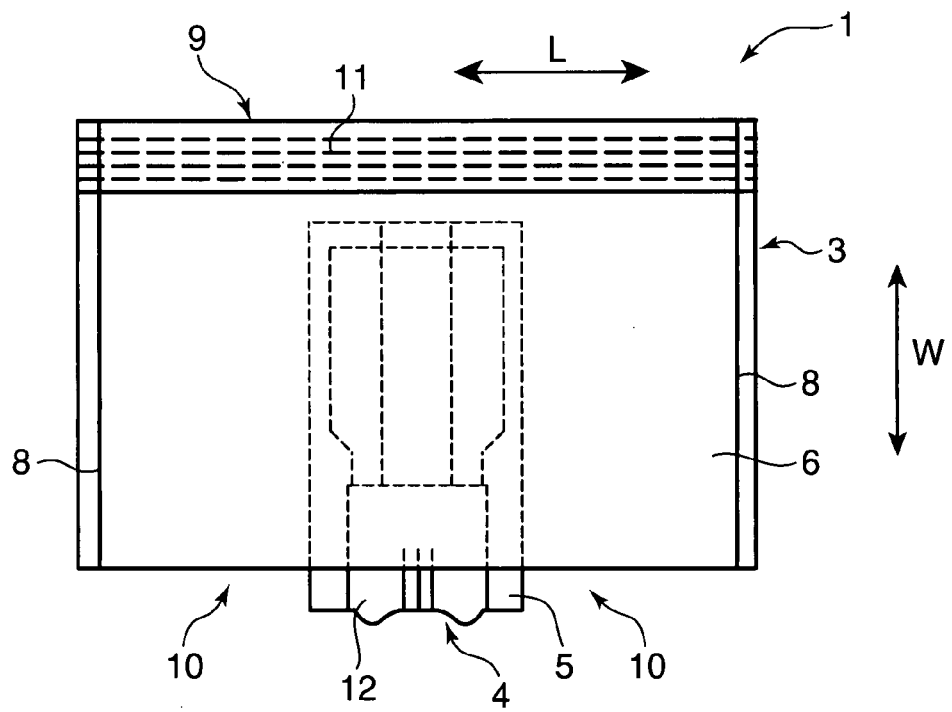
FIG. 1A is a plan view showing trunks-type disposable pants as an example of a wearing article of the invention.
Figure 1B:
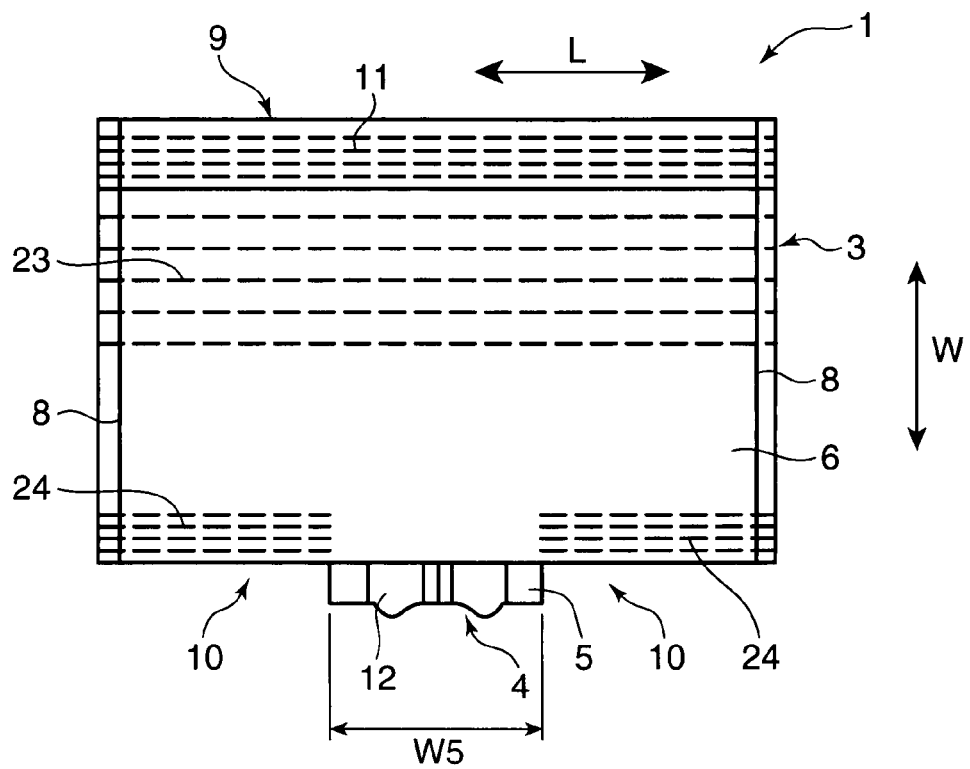
FIG. 1B is a plan view showing trunks-type disposable pants according to another embodiment.

FIG. 1A is a plan view showing trunks-type disposable pants 1 as an example of a wearing article of the invention, and FIG. 1B is a plan view showing trunks-type disposable pants 2 according to another embodiment.

FIG. 2 is a development view of the disposable pants 1 of FIG. 1A. FIG. 2A is a plan view, FIG. 2B is a side view of FIG. 2A, and FIG. 2C is a cross section taken on line C-C of FIG. 2A. An absorber 5 described below is indicated by a solid line in FIG. 2C and indicated by a virtual line in FIGS. 2A and 2B for ease of illustration.

Figure 3:
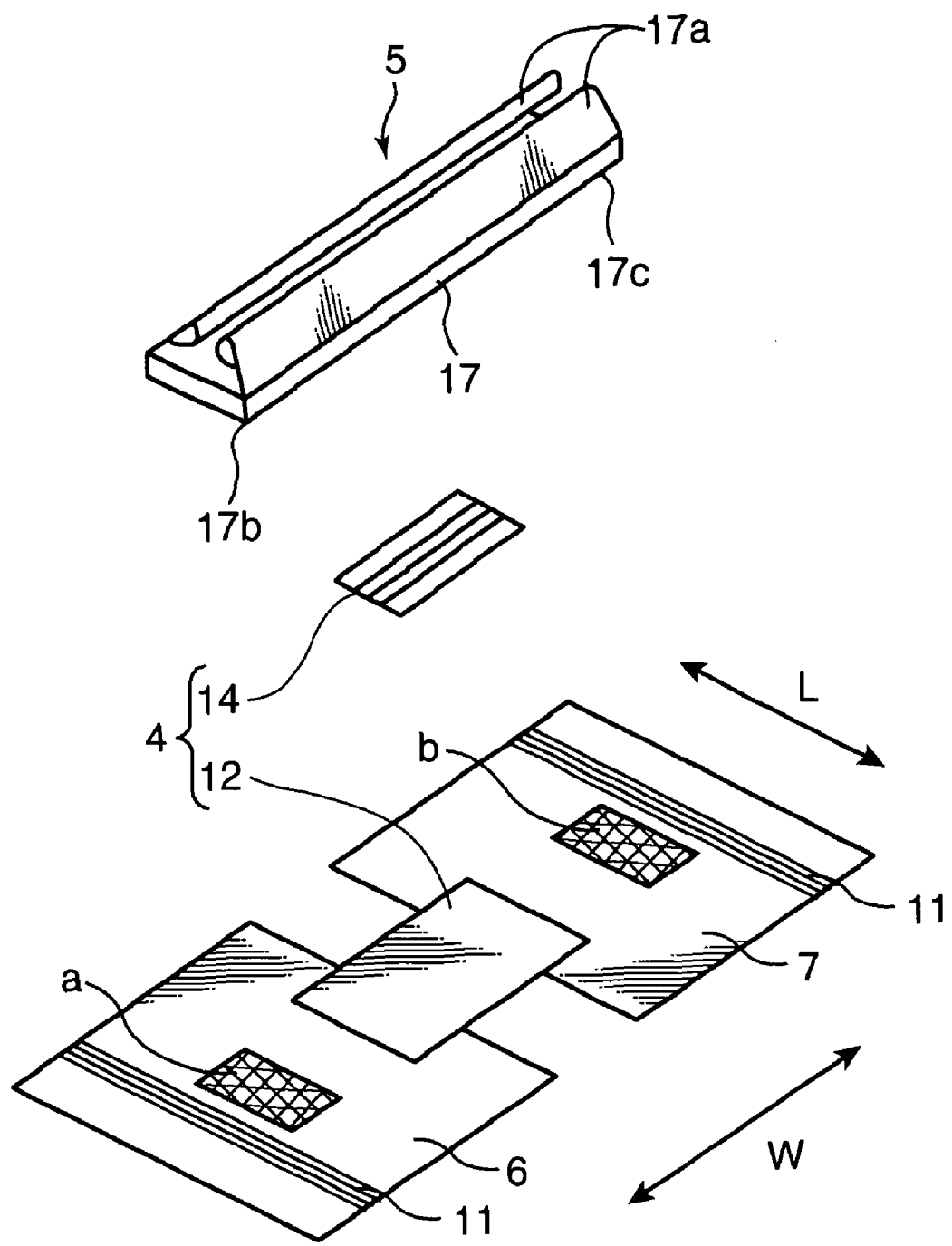
FIG. 3 is an exploded perspective view of the disposable pants of FIG. 1.

FIG. 3 is an exploded perspective view of the disposable pants 1 of FIG. 1.

Referring to the respective drawings, the disposable pants 1 include a waist portion 3 that continuously surrounds the waist of the wearer, a crotch portion 4 running under the crotch of the wearer, and the absorber 5 provided to cover the inner surface (skin surface side of the wearer) of the crotch portion 4.

The waist potion 3 includes a front portion 6 and a back portion 7 formed of rectangular non-woven cloths having substantially the equal areas, and the front portion 6 and the back portion 7 are joined to each other on the both edges in the longitudinal direction L with side seal portions 8 extending along the width direction W to form a ring shape.

Consequently, a pair of openings is made in the waist portion 3, and one of the openings (the upper opening in FIG. 1) is used as a waist opening 9.

Meanwhile, the crotch portion 4 is provided between the front portion 6 and the back portion 7 across the opening (the lower opening in FIG. 1) on the side opposite to the waist opening 9. The opening in the waist portion 3 is thus divided into two parts by the crotch portion 4 and these parts are used as leg openings 10.

In the disposable pants 1, because the opening in the waist portion 3 is divided into two parts by the crotch portion 4 and these parts are used as the leg openings 10, it is possible to form the respective leg openings 10 without the work to cut out the waist portion 3.

Hereinafter, a concrete configuration of the disposable pants 1 will be described.

A waist elastic member 11 in a stretched state is attached to the front portion 6 and the back portion 7 along the longitudinal direction L at the edges on the waist opening 9 side. As is shown in detail in FIG. 2B, the waist elastic member 11 is provided to the inner sides of the folded edges of the front portion 6 and the back portion 7.

The crotch portion 4 includes a crotch outer sheet 12 and a crotch elastic member 14 joined to the top surface (skin surface side of the wearer) of the crotch outer sheet 12, and it is folded between the front portion 6 and the back portion 7.

The both ends of the crotch outer sheet 12 are respectively joined to the front portion 6 and the back portion 7 while being bridged between the both portions 6 and 7 almost at the center positions in the longitudinal direction L.

The crotch elastic member 14 is attached to the crotch outer sheet 12 along the width direction W in a stretched state.

To be more concrete, as is shown in detail in FIG. 2C, the crotch elastic member 14 of this embodiment is bonded while being sandwiched between a pair of sheet material pieces 15 at top and bottom.

Figure 7:
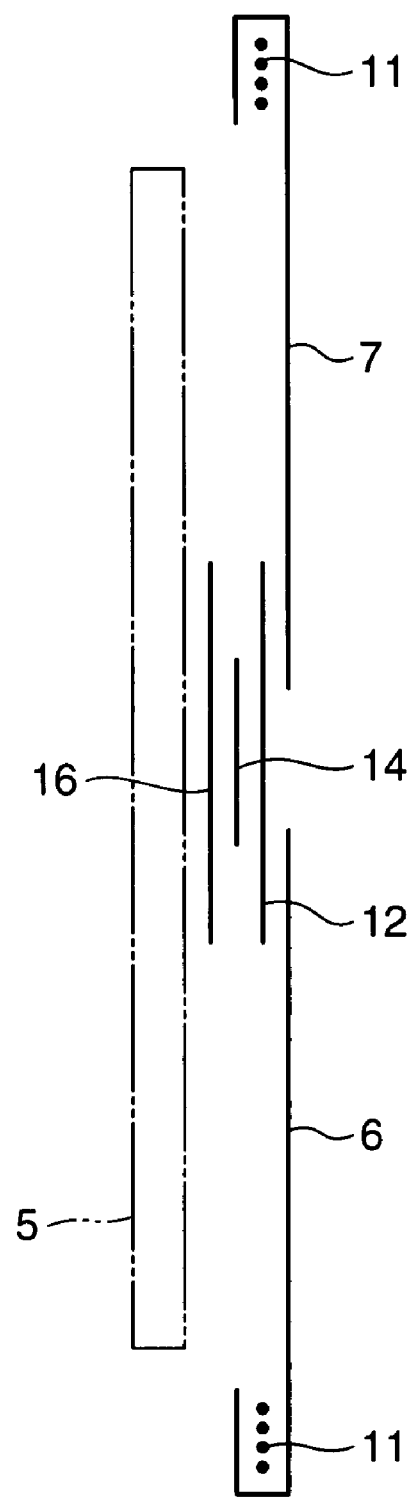
FIG. 7 is a side view showing another providing method of a crotch elastic member in the disposable pants of FIG. 2.

As is shown in FIG. 7, the crotch elastic member 14 may be bonded while being sandwiched between the crotch outer sheet 12 and a sheet material piece 16 of substantially the same shape as the sheet 12. Further, although it is not shown in the drawing, the crotch elastic member 14 may be bonded directly to the crotch outer sheet 12. The example shown in the drawing adopts the crotch elastic member 14 of a string shape. It is, however, possible to adopt a strip-shaped crotch elastic member.

A non-woven cloth or a film can be adopted as materials of the sheet material pieces 15 and 16. In a case where the crotch elastic member 14 is sandwiched between a pair of the sheet material pieces 15 as is shown in FIG. 2C, it is preferable to use a film for at least one of the sheet material pieces 15 in enhancing the workability. More specifically, by forming the sheet material piece 15 from a film, it becomes possible to transport the sheet material piece 15 by applying a suction pressure.

As is shown in FIG. 2, the length dimension Z over which the crotch elastic member 14 is disposed falls within a range of 40 mm to 350 mm in a stretched state. A range of 60 mm to 350 mm is suitable for the disposable pants 1 for adult and a range of 40 mm to 220 mm is suitable for the one for infant. The width dimension H of the crotch elastic member 14 is suitably about 70 mm at the maximum for both adult and infant. The stretching factor of the crotch elastic member 14 is 1.1 to 5.

By providing the crotch elastic member 14, shirring (corrugated shape formed by gathering a sheet material in folds, such as gathers, pleats, and creases) is formed in the crotch portion 4, and when put on the wearer, the crotch portion 4 is pulled upward (a direction toward the waist opening 9 from the leg openings 10) by the shirring and forms a gusset.

The shirring is formed in the crotch portion 4 at the center in the longitudinal direction L along the direction connecting the front portion 6 and the back portion 7 so as to shorten the interval between the front portion 6 and the back portion 7.

To be more concrete, as are shown in FIGS. 2A and 2B, the shirring is formed in a region having the width dimension H and the length dimension K (hereinafter, referred to as the shirring forming region). While the crotch elastic member 14 is in a stretched state (the state in FIG. 2), a ratio of the length dimension K of the shirring and a length L2 of the waist portion 3 from one waist edge to the opposing waist edge passing the crotch portion 4 is set to 1:15 to 1:2, and the ratio of K:L2 is preferably 1:4.4 to 1:3.8 to enhance the appearance of the disposable pants 1.

For those in the shapes of trunks and bloomers, a distance J between the edge of each leg opening 10 and the side edge of the shirring forming region is preferably 5 mm or greater.

As are shown in FIG. 2C and FIG. 3, the absorber 5 is made into a rectangular shape with the longitudinal direction thereof aligned with the width direction W. It is formed by sandwiching an absorbent core 19 between a fluid impermeable back sheet 17 and a fluid permeable top sheet 18, and rising flaps 17a are provided to the both sides.

The front part (the front part 17b of the back sheet 17) and the back part (the back part 17c of the back sheet 17) of the absorber 5 are attached, respectively, at fitting positions a and b of the disposable pants 1 indicated by cross-hatching when the need arises. The fitting method includes bonding using a hot melt bonding agent, a double-faced adhesive tape or the like, or alternatively, they can be laminated using a mechanical fastener or the like to enable replacement.

A part of the absorber 5 between the fitting positions a and b may not be fit to the crotch portion 4, and instead, it may be in a state floating from the part of the crotch elastic member 14 or placed along to come into contact with the crotch portion 4. Alternatively, it may be attached to the crotch portion 4 by the laminating method at the fitting positions a and b described above.

As has been described, according to the disposable pants 1, because the opening in the waist portion 3 is divided into two parts by the crotch portion 4 and these parts are used as the leg openings 10, it is possible to form the respective leg openings 10 without performing the work to cut out the waist portion 3.

Hence, according to the disposable pants 1, not only is it possible to reduce a loss of materials in comparison with a conventional wearing article that causes a loss of materials in an amount comparable to the opening areas of the leg openings 10, but it is also possible to reduce the cost of facilities because the facility needed for the work to cut out the leg openings 10 can be omitted.

Further, fastening occurs in the crotch portion 4 in the disposable pants 1 by the shirring formed in the crotch portion 4. The crotch portion 4 is therefore pulled upward and forms a gusset when put on the wearer, and the disposable pants 1 take on the shape of a trunks type. It is thus possible to achieve satisfactory wearing comfort and enhance the appearance when put on the wearer.

There is no intention to exclude the configuration to form the waist portion 3 from a single sheet of material. However, by configuring in such a manner that the waist portion 3 includes the front portion 6 and the back portion 7 separately as the embodiment described above, it is possible to form the disposable pants 1 by providing the crotch portion 4 across a space between the both portions 6 and 7 to be joined thereto, and then folding the crotch portion 4 so as to place the front portion 6 and the back portion 7 one on top of the other. The workability of the manufacturing work can be therefore enhanced in comparison with a case where a ring-shaped waist portion 3 is formed from a single sheet of material and the crotch portion 4 is joined thereto across the opening thereof.

As in the embodiment described above, by forming the shirring held in a corrugated shape made by being gathered in folds in the direction connecting the front portion 6 and the back portion 7, fastening occurs in the crotch portion 4. The crotch portion 4 is therefore pulled upward and forms a gusset, and the disposable pants 1 can take on the shape of a trunks type.

As in the embodiment described above, by forming the shirring using a stretching and shrinkage force of the crotch elastic member 14, fastening occurs in the crotch portion 4. The crotch portion 4 is therefore pulled upward and forms a gusset and the disposable pants 1 can take on the shape of a trunks type. Further, the gusset formed by the crotch elastic member 14 lets the crotch portion 4 fit to the crotch of the wearer tightly and elastically, which can enhance the wearing comfort.

In the embodiment described above, because a ratio of the length dimension K of the shirring in a stretched state and the length dimension L2 between the waist edges of the front portion 6 and the back portion 7 passing the crotch portion 4 is set to 1:15 to 1:2, it is possible to form the disposable pants 1 in the shape of trunks with good appearance.

Further, in the embodiment described above, because it is configured in such a manner that the gusset is formed in the crotch portion 4 by the shirring when put on the wearer, it is possible to hold the shape of the corrugated part in the manufacturing line with ease at low costs.

By configuring to provide the absorber 12 as in the embodiment described above, it possible to use the disposable pants 1 as pants-type diapers for infant, training pants, or incontinence pants for adult.

In the embodiment described above, the absorber 5 covers the crotch portion 4 entirely. However, the crotch outer sheet 12 of the crotch portion 4 may be formed wider than the absorber 5 along the longitudinal direction L for the absorber 5 to be disposed on the crotch outer sheet 12.

Figure 4:
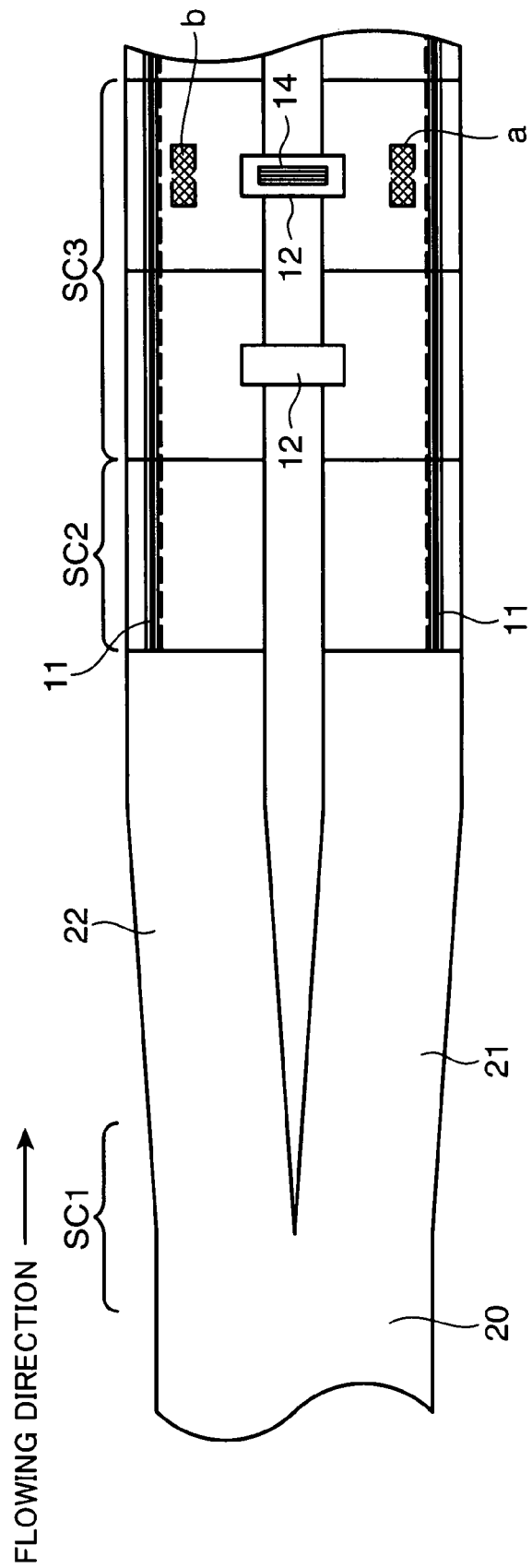
FIG. 4 is a plan view schematically showing the first half of a method of manufacturing the disposable pants of FIG. 1A.
Figure 5:
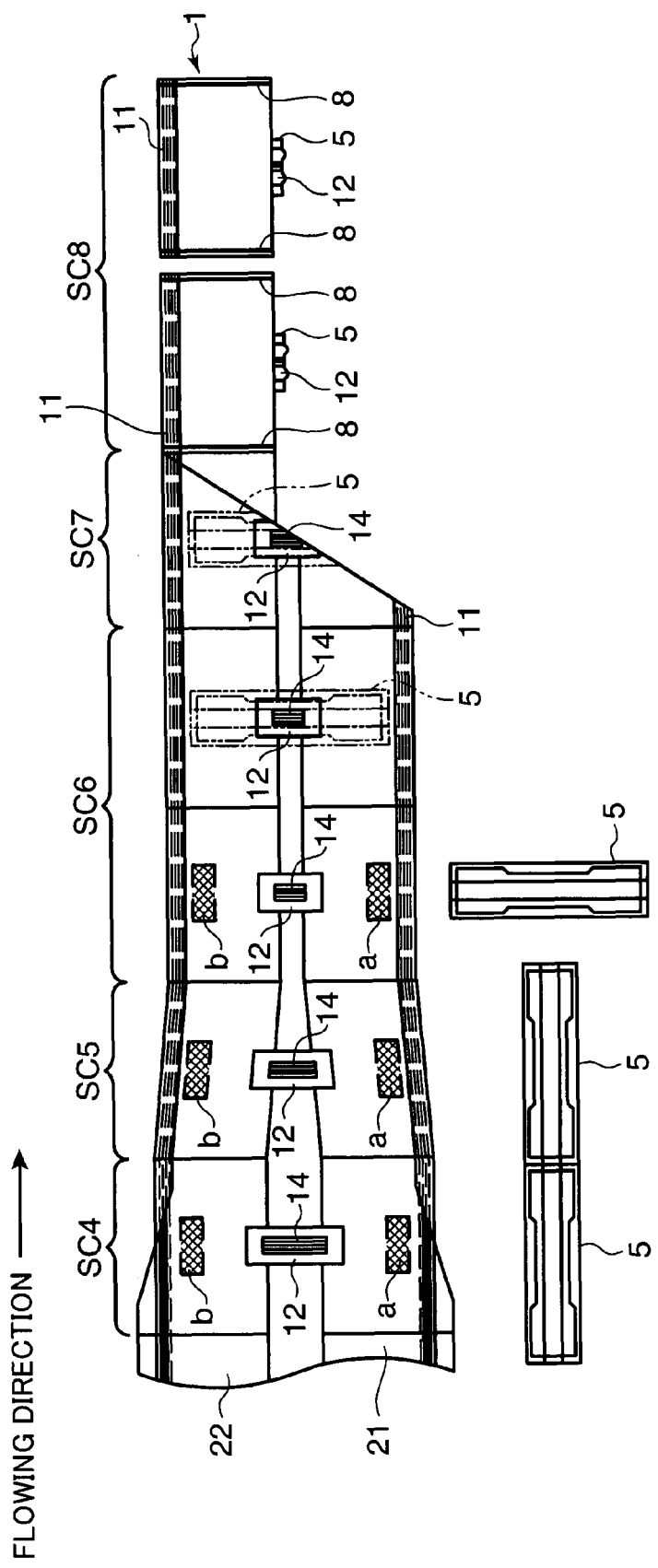
FIG. 5 is a plan view schematically showing the second half of the method of manufacturing the disposable pants of FIG. 1A.

The disposable pants 1 can be manufactured along the manufacturing line as shown in FIG. 4 and FIG. 5.

In the manufacturing line, a cut-opening section SC1, an elastic member attaching section SC2, a joining section SC3, an edge folding section SC4, a width narrowing section SC5, an absorber joining section SC6, a folding section SC7, and a cutting section SC8 are set sequentially from the upstream in the flowing direction.

In the cut-opening section SC1, a strip-shaped web 20 being transported along the flowing direction is cut into two almost equal parts in the width direction to form a front outer web 21 and a back outer web 22 (hereinafter, occasionally referred to as the both outer webs 21 and 22).

The front outer web 21 is cut to have the width dimension, which is a sum of a width dimension W1 of the front portion 6 shown in FIG. 2 and a dimension W2 folded in an edge folding step described below.

Likewise, the back outer web 22 is cut to have the width dimension, which is a sum of a width dimension W3 of the back portion 7 shown in FIG. 2 and a dimension W4 folded in the edge folding step described below.

In short, the web 20 of this embodiment is set to have the width dimension found to be (W1+W2+W3+W4).

The front outer web 21 and the back outer web 22 are transported along the flowing direction in parallel with each other while being spaced apart by a specific interval (front outer web transporting step and back outer web transporting step).

In the elastic member attaching section SC2, the waist elastic member 11 in a stretched state is attached to the front outer web 21 and the back outer web 22 along the flowing direction at the edges spaced apart from each other (waist elastic member attaching step).

In the waist elastic member attaching step, the long waist elastic member 11 is joined onto the both outer webs 21 and 22 continuously along the flowing direction.

In the joining section SC3, the crotch outer sheet 12 is disposed so as to bridge between the both outer webs 21 and 22, and the crotch outer sheet 12 is then joined to the both outer webs 21 and 22 separately (joining step).

Further, in the joining step, the crotch elastic member 14 in a stretched state is attached to the crotch outer sheet 12 along a direction orthogonal to the flowing direction (attaching step). An attaching method of the crotch elastic member 14 may be any of a method of joining the one sandwiched between a pair of the sheet material pieces 15 at top and bottom shown in FIG. 2B to the crotch outer sheet 12, a method of sandwiching the one between the crotch outer sheet 12 and the sheet material piece 16 as shown in FIG. 7, and a method of directly bonding the one to the crotch outer sheet 12.

Also, in the joining step, the crotch elastic member 14 sandwiched between the crotch outer sheet 12 and the sheet material piece 16 in advance as is shown in FIG. 7 or the crotch elastic member 14 bonded directly to the crotch outer sheet 12 in advance may be joined onto the both outer webs 21 and 22.

In the edge folding section SC4, the edges of the both outer webs 21 and 22 on the sides spaced apart from each other are folded inside by the folding dimensions W2 and W4 shown in FIG. 2 so as to sandwich the waist elastic member 11, and the folded edges are joined to the both outer webs 21 and 22 separately (edge folding step).

In the width narrowing section SC5, the interval between the both outer webs 21 and 22 is narrowed in response to a shrinkage force of the crotch elastic member 14 (width narrowing step). More specifically, in the width narrowing step, the interval between the both outer webs 21 and 22 is narrowed to an interval matching the natural length of the crotch elastic member 14 by releasing the holding force conferred to the both outer webs 21 and 22 to maintain the crotch elastic member 14 in a stretched state.

That is to say, according to the manufacturing method of this embodiment, the shirring gathered in folds in the direction orthogonal to the flowing direction is formed on the crotch outer sheet 12 by joining the crotch elastic member 14 onto the crotch outer sheet 12 in the joining step and by letting the crotch outer sheet 12 shrink in the orthogonal direction by utilizing the shrinkage force of the crotch elastic member 14 in the width narrowing step. In short, the process including the joining step and the width narrowing step forms an example of the shirring forming step of this embodiment.

It should be appreciated, however, that the shirring forming step is not limited to the one including the joining step and the width narrowing step. For example, the shirring may be formed on the crotch outer sheet 12 by holding the crotch outer sheet 12 in the conformation when it was let to shrink in the direction orthogonal to the flowing direction in the width narrowing step.

To be more concrete, by laminating a sheet material piece separately on almost the entire top surface of the crotch outer sheet 12 gathered in folds in the orthogonal direction in the width narrowing step, it is possible to hold the conformation of the part gathered in folds formed in the crotch outer sheet 12 as the shirring. The part gathered in folds can be made into any desired shape by letting the crotch outer sheet 12 pass through a space between a pair of embossing rollers having the concavo-convex surfaces that fit in each other.

In the absorber joining section SC6, the absorber 5 transported in parallel with the both outer webs 21 and 22 in a posture such that aligns the longitudinal direction thereof with the flowing direction is rotated by 90° and is disposed so as to cover the top surface of the crotch outer sheet 12. The absorber 5 is then joined to the both outer webs 21 and 22 at the fitting positions a and b, respectively (absorber joining step).

In the folding section SC7, the crotch portion 4 and the absorber 5 are folded to place the both outer webs 21 and 22 one on top of the other (folding step). In other words, in this folding step, the edges of the both outer webs 21 and 22 to which is provided the waist elastic member 11 are placed one on top of the other.

In the cutting section SC8, a pair of side seal portions 8 is formed by joining the both outer webs 21 and 22 along the width direction of the both outer webs 21 and 22 at positions having the crotch outer sheet 12 in between, and both the outer webs 21 and 22 are cut so as to include the both side seal portions 8 (cutting step).

In this cutting step, the waist elastic member 11 is cut as well, and the disposable pants 1 are manufactured.

Figure 6:
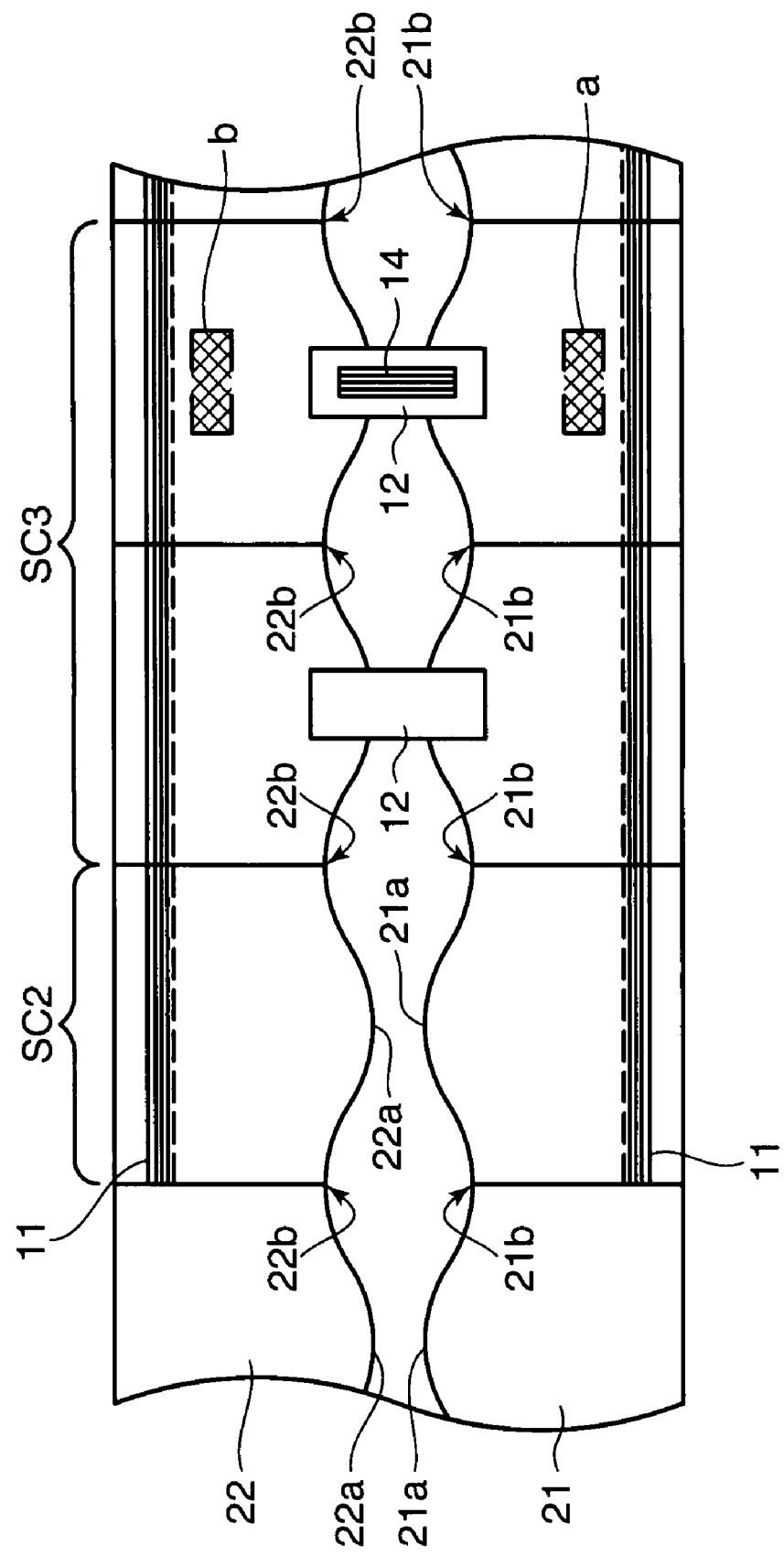
FIG. 6 is a plan view schematically showing another embodiment of a cut-opening step of FIG. 4.

The web 20 is cut open linearly in the cut-opening section SC1 of this embodiment. The invention, however, is not limited to this embodiment, and for example, as is shown in FIG. 6, it may be cut open in the shape of a capital S.

In this case, the both outer webs 21 and 22 are transported by shifting the phases (positions) so that the crests 21a and 22a as well as troughs 21b and 22b of the both outer webs 21 and 22 oppose each other in the front outer web transporting step and the back outer web transporting step.

When configured in this manner, the completed disposable pants 1 are pants of a shape in which the sides of the thighs are cut up around.

Alternatively, the web 20 may be cut open linearly in the cut-opening section SC1, and notches corresponding to the crests 21a and 22a may be formed later, respectively, in the front outer web 21 and the back outer web 22 formed in this section.

Further, as with the disposable pants 2 of FIG. 1B, it is possible to provide a body-fitting elastic member 23 and a leg elastic member 24 to the front portion 6 and the back portion 7 of the disposable pants 1 of the embodiment described above.

The body-fitting elastic member 23 is attached in a stretched state along a direction almost parallel to the waist elastic member 11 so as to let the front portion 6 and the back portion 7 fit tightly around the waist.

The leg elastic member 24 is attached in a stretched state along the edge of each leg opening 10 in the front portion 6 and the back portion 7. The leg elastic member 24 tightens the leg openings 10 to let the edges thereof fit tightly around the legs of the wearer.

It should be noted that the leg elastic member 24 is not provided to a region for the absorber 5 having a width dimension W5. This configuration suppresses shrinkage of the absorber 5 caused by a shrinkage force of the leg elastic member 24.

As has been described, according to the method of manufacturing the disposable pants 1 described above, it is possible to manufacture the disposable pants 1 in which both the outer webs 21 and 22 are joined in a ring shape while one of the openings is divided into two parts by the crotch outer sheet 12 by providing the crotch outer sheet 12 across a space between the front outer web 21 and the back outer web 22, and joining the both outer webs 21 and 22 placed one on top of the other by folding the crotch outer sheet 12 on the both sides of the crotch outer sheet 12.

In other words, according to this manufacturing method, because clearances corresponding to the leg openings 10 can be formed on the both sides of the crotch outer sheet 12 by joining the crotch outer sheet 12 to the strip-shaped front outer web 21 and the strip-shape back outer web 22 across a space therebetween, it is possible to form the leg openings 10 without performing the work to cut out the both outer webs 21 and 22.

Hence, according to the manufacturing method described above, not only is it possible to reduce a loss of materials in comparison with the conventional disposable pants 1 that cause a loss of materials in an amount comparable to the opening areas of the leg openings 10, but it is also possible to reduce the cost of facilities because the facility needed for the work to cut out the leg openings 10 can be omitted.

Further, according to the manufacturing method described above, because the shirring is formed in the crotch outer sheet 12 along the direction crossing the flowing direction, fastening occurs in the crotch portion 4 in the completed disposable pants 1 due to the shirring formed in the crotch portion 4 (crotch outer web). The crotch portion 4 is therefore pulled upward and forms a gusset when put on the wearer, and the disposable pants 1 take on the shape of a trunks type. It is thus possible to achieve satisfactory wearing comfort and enhance the appearance when put on the wearer.

According to the manufacturing method including the waist elastic member attaching step as in the embodiment described above, because the waist opening 9 formed between the front outer web 21 and the back outer web 22 can be tightened by the waist elastic member 11, it is possible to suppress the slipping down when put on the wearer by letting the waist opening 10 fit tightly around the waist of the wearer.

According to the manufacturing method including the cut-opening step as in the embodiment described above, because it is possible to form the front outer web 21 and the back outer web 22 from the common web 20, in comparison with a case where the both outer webs 21 and 22 are prepared separately, the basic unit can be increased for a single web material, which makes it possible to reduce the manufacturing costs.

According to the manufacturing method configured so as to dispose the crotch elastic member 14 along the width direction of the both outer webs 21 and 22 in the joining step as in the embodiment described above, because the crotch elastic member 14 is disposed so as to bridge between the front outer web 21 and the back outer web 22, it is possible to form the shirring in the crotch outer sheet 12 as the crotch outer sheet 12 shrinks due to a shrinkage force of the crotch elastic member 14. Consequently, in the completed disposable pants 1, a gusset is formed between the front portion 6 (front outer web 21) and the back portion 7 (back outer web 22) as the crotch portion 4 (crotch outer sheet) is pulled upward by the shirring. Hence, according to this manufacturing method, it is possible to manufacture the disposable pants 1 with good wearing comfort by letting the crotch portion 4 fit to the crotch of the wearer tightly and elastically by the gusset.

According to the embodiment described above, it is possible to form the shirring by a work as simple as gathering the crotch outer sheet 12 by narrowing the interval between the front outer web 21 and the back outer web 22 and holding the conformation of the crotch outer sheet 12 in this instance.

According to the manufacturing method including the width narrowing step and the absorber joining step as in the embodiment described above, because the absorber 5 is provided onto the crotch outer sheet 12 after the interval between the front outer web 21 and the back outer web 22 is narrowed, it is possible to form the shirring in the crotch outer sheet 12 while maintaining the absorber 5 in its natural length.

In the manufacturing method according to the embodiment described above, the absorber joining step is performed after the width narrowing step. However, the crotch elastic member 14 may be maintained in a stretched state at least until the absorber joining step is completed after the attaching step (joining step).

Figure 8:
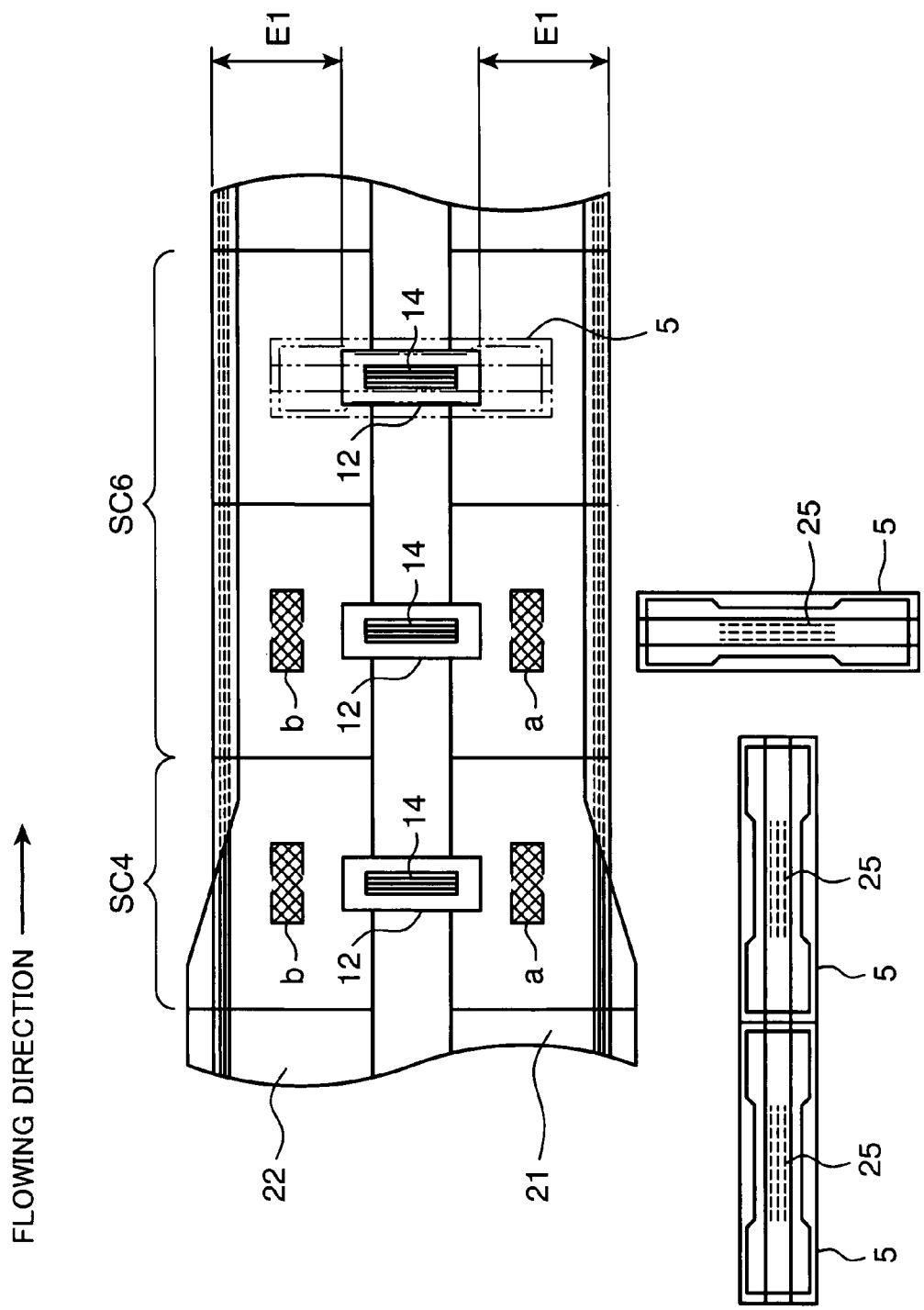
FIG. 8 is a plan view schematically showing a method of manufacturing disposable pants according to another embodiment of the invention.

To be more concrete, as is shown in FIG. 8, after the crotch elastic member (first crotch elastic member) 14 is joined onto the crotch outer sheet 12 (attaching step, see FIG. 4) in the joining section SC3, the edges of the both outer webs 21 and 22 are folded in the edge folding section SC4 while the crotch elastic member 14 is maintained in a stretched state (maintaining step), and the absorber 5 is joined so as to bridge between the both outer sheets 21 and 22 in the absorber joining section SC6 (absorber joining step), after which the folding step and the cutting step (see FIG. 5 for each step) can be performed in the same manner as with the embodiment described above.

When configured in this manner, because the absorber 5 can be disposed onto the both outer webs 21 and 22 while the crotch elastic member 14 is maintained in a stretched state, different from a case where the crotch elastic member 14 has shrunk and the absorber 5 is disposed while the both outer webs 21 and 22 are close to each other, it is possible to position the absorber 5 onto the both outer webs 21 and 22 at a higher degree of accuracy.

Further, as is shown in FIG. 8, it is possible to attach a second crotch elastic member 25 in a stretched state to the absorber 5. Then, in the absorber joining step, the absorber 5 is disposed in such a manner that the longitudinal direction of the second crotch elastic member 25 aligns with a direction orthogonal to the flowing direction and joined to the both outer webs 21 and 22 while the second crotch elastic member 25 is maintained in a stretched state.

Figure 9:
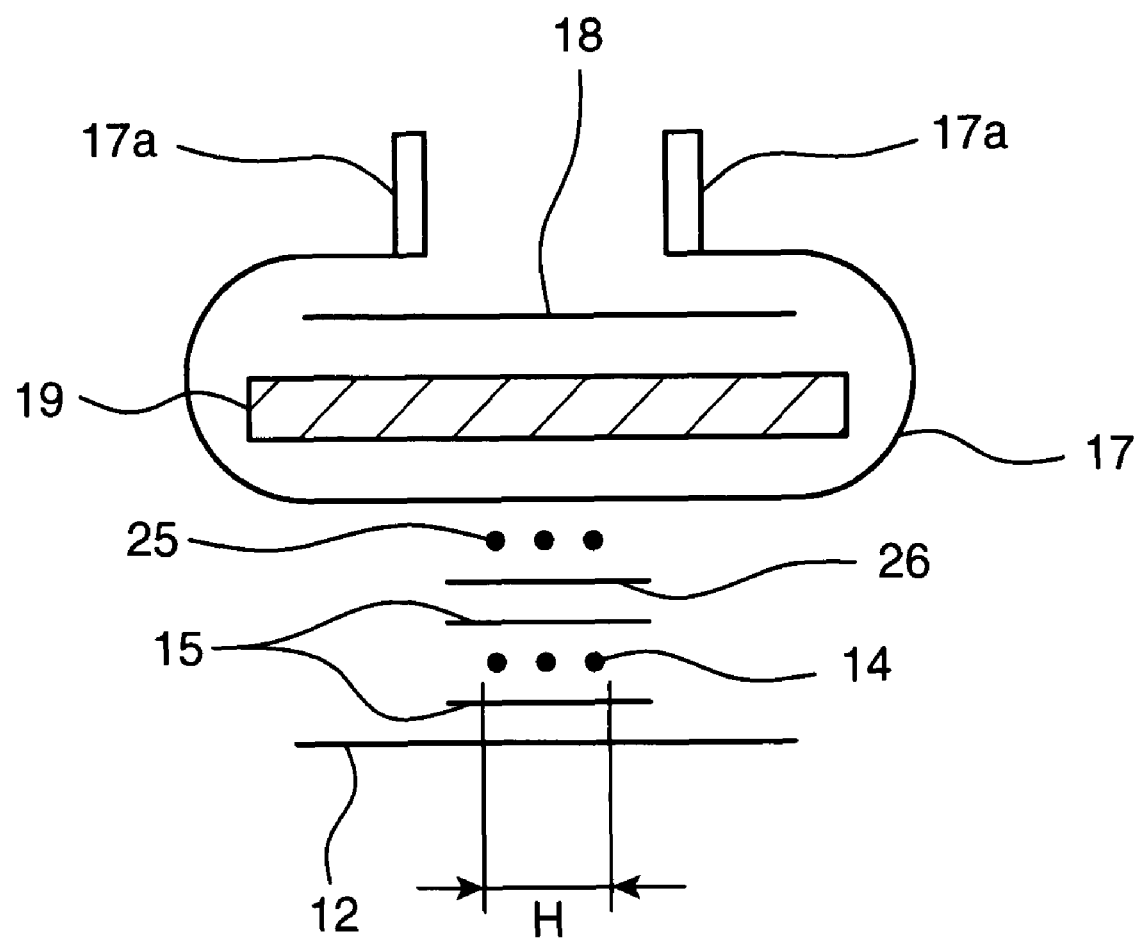
FIG. 9 is a view corresponding to FIG. 2C and showing disposable pants according to still another embodiment of the invention.

To be more concrete, as is shown in FIG. 9, the second crotch elastic member 25 is bonded while being sandwiched between the back sheet 17 of the absorber 5 and a sheet material piece 26 provided on the outside of the back sheet 17. Although it is not shown in the drawing, the second crotch elastic member 25 may be directly bonded to the top surface or the bottom surface of the back sheet 17.

When configured in this manner, it is also possible to let the absorber 5 shrink. Hence, by letting the absorber 5 and the crotch elastic member 14 shrink integrally, the both outer webs 21 and 22 as well as the absorber 5 in the completed disposable pants 1 are allowed to fit to the crotch of the wearer.

Further, according to the method described above, because fastening occurs in the absorber 5 due to the shrinkage force of the second crotch elastic member 25 in the completed disposable pants 1, the absorber 5 is pulled upward when put on the wearer, which further enhances the wearing comfort when put on the wearer.

In addition, according to the methods of the respective embodiments described above, the edges of the both outer webs 21 and 22 in the width direction on the sides spaced part from each other are left as non-attachment regions E1 (see FIG. 8) where the crotch elastic member 14 (the crotch outer sheet 12) is not provided, and the fitting positions a and b for the absorber 5 are set in the non-attachment regions E1. Hence, because the crotch outer sheet 12 is allowed to stretch and shrink independently of the absorber 5 in the region where the crotch elastic member 14 is attached, it is possible to provide the gusset in the crotch portion of the completed disposable pants 1 regardless of the stiffness (stretching and shrinking) of the absorber 5.

Further, in a case where the second crotch elastic member 25 is also attached to the absorber 5 in a state where the non-attachment regions E1 are set, because the absorber 5 is allowed to fit to the crotch of the wearer without influences of the stretching and shrinking of the crotch elastic member 14 in the completed disposable pants 1, it is possible to achieve more satisfactory wearing comfort.

The respective embodiments described above described the technique of using the clearances formed between the front outer web 21 and the back outer web 22 directly as the leg openings 10. It should be appreciated, however, that there is no intention to limit the invention to a case where no working is applied to the front outer web 21 and the back outer web 22.

Figure 10:
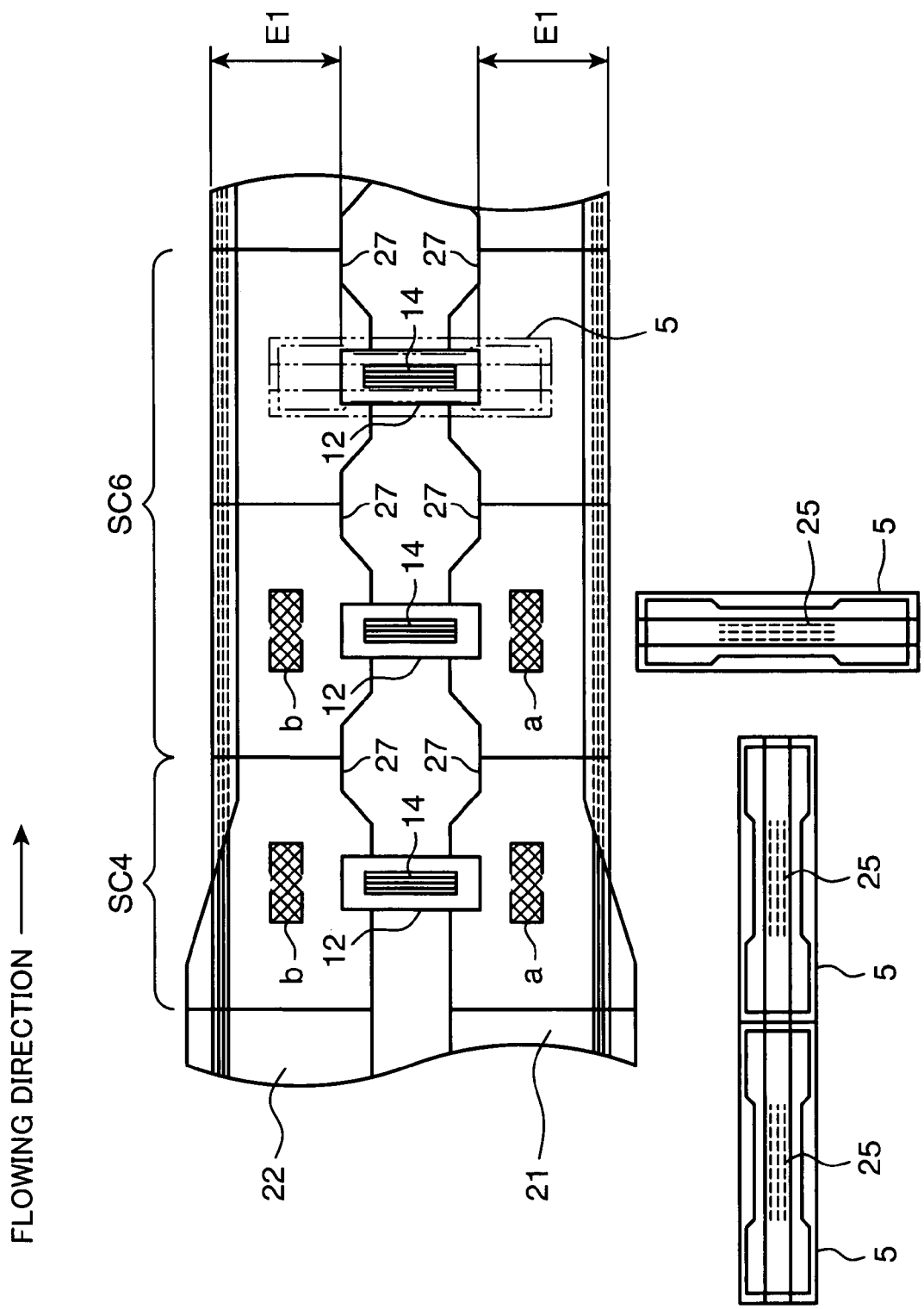
FIG. 10 is a plan view schematically showing a method of manufacturing disposable pants according to still another embodiment of the invention.

More specifically, it is possible to form the disposable pants 1 in which the leg openings 10 are cut in toward the waist opening 9 by forming notches 27 (see FIG. 10) in the front outer web 21 and the back outer web 22 at the edges in close proximity to each other.

The planar shape of the notches 27 can be of various shapes, such as a circular arc shape, a square shape, and a triangular shape.

Even when configured in this manner, in comparison with the conventional technique of forming leg openings merely by the punching work, it is possible to make the area of a cut-out piece smaller by an amount comparable to the clearances between the front outer web 21 and the back outer web 22, which makes it possible to reduce a loss of materials.

More specifically, the invention in the embodiments described above provides a wearing article, characterized by including a waist portion formed in a ring shape capable of continuously surrounding a waist of a wearer and using one of openings as a waist opening, and a crotch portion joined to the waist portion across an opening on an opposite side to the waist opening so that the crotch portion and the waist portion define a pair of leg openings for the wearer to put through his legs individually, wherein the crotch portion is formed with shirring in which the crotch portion is let to shrink in a direction in which mutually opposing inner surfaces of the waist portion come closer to each other.

According to the invention, because the opening in the waist portion is divided into two parts by the crotch portion and these parts are used as leg openings, it is possible to form the respective leg openings without the work to cut out the waist portion.

Hence, according to the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, the fastening occurs in the crotch portion by the shirring (corrugated shape formed by gathering a sheet material in folds, such as gathers, pleats, and creases) formed in the crotch portion. The crotch portion is therefore pulled upward (in a direction toward the waist opening from the leg openings) and forms a gusset when put on the wearer, and the wearing article takes on the shape of a trunks type. It is thus possible to achieve satisfactory wearing comfort and enhance the appearance when put on the wearer.

In the wearing article described above, it is preferable that: the waist portion separately includes a front portion disposed on an abdomen of the wearer and a back portion disposed on a back of the wearer; the front portion and the back portion are joined to each other in a ring shape; and the shirring is formed to shorten an interval between the front portion and the back portion.

According to this configuration, because the waist portion includes the front portion and the back portion separately, it is possible to manufacture a wearing article by providing the crotch portion across a space between the both portions and joining the crotch portion to the both portions, and folding the crotch portion to place the front portion and the back portion one on top of the other. The workability of the manufacturing work can be therefore enhanced in comparison with a case where a ring-shaped waist portion is formed from a single sheet of material and the crotch portion is joined to the waist portion across the opening thereof.

In the wearing article described, above, it is preferable that the shirring is formed by gathering the crotch portion in folds in a direction connecting the inner surfaces of the waist portion to held in a corrugated shape.

According to this configuration, by holding the crotch portion in a corrugated shape while being gathered in folds in the direction connecting the inner surfaces of the waist portion, fastening occurs in the crotch portion. The crotch portion is therefore pulled upward and forms a gusset, and the wearing article can take on the shape of a trunks type.

In the wearing article described above, it is preferable that the shirring is formed by a shrinkage force of a crotch elastic member attached in a stretched state to the crotch portion along a direction connecting the inner surfaces of the waist portion.

According to this configuration, by forming the shirring using a shrinkage force of the crotch elastic member, fastening occurs in the crotch portion. The crotch portion is therefore pulled upward and forms a gusset, and the wearing article can take on the shape of a trunks type. Further, by letting the crotch portion fit to the crotch of the wearer tightly and elastically by the gusset formed by the crotch elastic member, the wearing comfort can be enhanced.

In the wearing article described above, it is preferable that for the shirring in a stretched state, a ratio of a length dimension of the shirring and a length dimension of the waist portion from a waist edge to an opposing waist edge passing the crotch portion is 1:15 to 1:2.

According to this configuration, because the ratio of the length dimension of the shirring and the length dimension of the waist portion from the waist edge to the opposing waist edge passing the crotch portion is set to 1:15 to 1:2, the wearing article can be formed in the shape of trunks with good appearance.

In the wearing article described above, it is preferable that a gusset is formed in the crotch portion by the shirring when the wearing article is put on the wearer.

According to this configuration, it is possible to hold the shape of the corrugated part in the manufacturing line with ease at low costs.

In the wearing article described above, it is preferable to further include an absorber provided to cover an inner surface of the crotch portion, and it is preferable that at least both ends of the absorber are joined to the mutually opposing inner surfaces of the waist portion.

According to this configuration, the wearing article can be used as pants-type diapers for infant, training pants, and incontinence pants for adult.

Also, the invention provides a method of manufacturing a wearing article having a front portion disposed on an abdomen of a wearer and a back portion disposed on a back of the wearer, characterized by including: a front outer web transporting step of transporting a strip-shaped front outer web used to form the front portion in such a manner that a longitudinal direction thereof aligns with a pre-set flowing direction; a back outer web transporting step of transporting a strip-shaped back outer web used to form the back portion in parallel with the front outer web with a specific interval from the front outer web; a joining step of disposing a crotch outer sheet so as to bridge between the both outer webs and joining the crotch outer sheet onto the both outer webs; a shirring forming step of forming shirring in the crotch outer sheet along a direction crossing the flowing direction; a folding step of placing the front outer web and the back outer web one on top of the other by folding the crotch outer sheet; and a cutting step of joining the front outer web and the back outer web along a width direction of the both outer webs at positions on both sides of the crotch outer sheet and cutting the both outer webs for every wearing article.

According to the invention, it is possible to manufacture a wearing article in which the both outer webs are joined in a ring shape and one of the openings is divided into two parts by the crotch outer sheet by providing the crotch outer sheet across a space between the front outer web and the back outer web and by joining the both outer webs placed one on top of the other by folding the crotch outer sheet on the both sides of the crotch outer sheet.

More specifically, according to the manufacturing method described above, because clearances corresponding to the leg openings can be formed on the both sides of the crotch outer sheet by joining the crotch outer sheet to the strip-shaped front outer web and the strip-shaped back outer web across a space therebetween, it is possible to form the leg openings without performing the work to cut out the both outer webs.

Hence, according to the manufacturing method of a wearing article of the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, because the shirring is formed in the crotch outer sheet along the direction crossing the flowing direction, the fastening occurs in the crotch portion in the completed wearing article by the shirring formed in the crotch portion (crotch outer web). The crotch portion is therefore pulled upward and forms a gusset when put on the wearer, and the wearing article takes on the shape of a trunks type. It is thus possible to achieve satisfactory wearing comfort and enhance the appearance when put on the wearer.

In the invention, the phrase, "cut the both outer webs for every wearing article", means to cut the outer webs for every region including a pair of joined parts formed on the both sides of the crotch outer sheet.

In the method of manufacturing a wearing article described above, it is preferable to further include a cut-opening step of forming the front outer web and the back outer web from a common web by cutting the common web.

According to this configuration, because the front outer web and the back outer web can be formed from a common web, in comparison with a case where the both outer webs are prepared separately, the basic unit can be increased for a single web material, which makes it possible to reduce the manufacturing costs.

In the method of manufacturing a wearing article described above, it is preferable that: a crotch elastic member in a stretched state is attached to the crotch outer sheet; the crotch elastic member is disposed along the width direction of the front outer web and the back outer web in the joining step; and the shirring is formed by narrowing the interval between the front outer web and the back outer web in response to a shrinkage force of the crotch elastic member in the shirring forming step.

According to this configuration, because the crotch elastic member is disposed so as to bridge between the front outer web and the back outer web, it is possible to form the shirring in the crotch outer sheet by letting the crotch outer sheet shrink by a shrinkage force of the crotch elastic member. Consequently, in the completed wearing article, the crotch portion (crotch outer sheet) is pulled upward by the shirring, and a gusset is formed between the front portion (front outer web) and the back portion (back outer web). Hence, according to this method, it is possible to manufacture a wearing article achieving satisfactory wearing comfort by letting the crotch portion fit to the crotch of the wearer tightly and elastically by the gusset.

In the method of manufacturing a wearing article described above, it is preferable that the shirring is formed by narrowing the interval between the front outer web and the back outer web and holding a conformation in this instance in the shirring forming step.

According to this configuration, it is possible to form the shirring by a work as simple as gathering the crotch outer sheet by narrowing the interval between the front outer web and the back outer web and holding the conformation of the crotch outer sheet in this instance.

It is preferable to further include an absorber joining step of disposing an absorber so as to cover a top surface of the crotch outer sheet after the interval between the front outer web and the back outer web is narrowed in the shirring forming step and joining at least the absorber to the front outer web and the back outer web.

According to this configuration, because the absorber is provided on the crotch outer sheet after the interval between the front outer web and the back outer web is narrowed, it is possible to form the shirring in the crotch outer sheet while maintaining the absorber in its natural length.

Also, the invention provides a method of manufacturing a wearing article having a front portion disposed on an abdomen of a wearer and a back portion disposed on a back of the wearer, characterized by including: a front outer web transporting step of transporting a strip-shaped front outer web used to form the front portion in such a manner that a longitudinal direction thereof aligns with a pre-set flowing direction; a back outer web transporting step of transporting a strip-shaped back outer web used to form the back portion in parallel with the front outer web with a specific interval from the front outer web; an outer sheet joining step of disposing a crotch outer sheet so as to bridge between the both outer webs and joining the crotch outer sheet onto the both outer webs; an attaching step of attaching a first crotch elastic member in a stretched state to the crotch outer sheet in a direction crossing the flowing direction; a maintaining step of maintaining the first crotch elastic member in the stretched state; a folding step of placing the front outer web and the back outer web one on top of the other by folding the crotch outer sheet; and a cutting step of joining the front outer web and the back outer web along a width direction of the both outer webs at positions on both sides of the crotch outer sheet and cutting the both outer webs for every wearing article.

According to the invention, it is possible to manufacture a wearing article in which the both outer webs are joined in a ring shape and one of the openings is divided into two parts by the crotch outer sheet by providing the crotch outer sheet across a space between the front outer web and the back outer web and by joining the both outer webs placed one on top of the other by folding the crotch outer sheet on the both sides of the crotch outer sheet.

More specifically, according to the manufacturing method described above, because clearances corresponding to the leg openings can be formed on the both sides of the crotch outer sheet by joining the crotch outer sheet to the strip-shaped front outer web and the strip-shaped back outer web across a space therebetween, it is possible to form the leg openings without performing the work to cut out the both outer webs.

Hence, according to the method of manufacturing a wearing article of the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

Further, according to the invention, because the first crotch elastic member in a stretched state can be attached to a region that will be made into the crotch portion when the wearing article is completed, fastening occurs in the crotch portion due to a shrinkage force of the first crotch elastic member in the completed wearing article. The crotch portion is therefore pulled upward and forms a gusset when put on the wearer, and the wearing article takes on the shape of a trunks type. It is thus possible to achieve satisfactory wearing comfort and enhance the appearance when put on the wearer.

In the method of manufacturing a wearing article described above, it is preferable to further include an absorber joining step of disposing an absorber so as to cover the first crotch elastic member and joining the absorber at least to top surfaces of the front outer web and the back outer web while the maintaining step is performed.

According to this configuration, because the absorber can be disposed onto the both outer webs while the first crotch elastic member is maintained in a stretched state, different from a case where the first crotch elastic member has shrunk and the absorber is disposed while the both outer webs are close to each other, it is possible to position the absorber onto the both outer webs at a higher degree of accuracy.

It is preferable that a second crotch elastic member in a stretched state is attached to the absorber, and the second crotch elastic member is disposed in such a manner that a longitudinal direction thereof aligns with the direction crossing the flowing direction in the absorber joining step.

When configured in this manner, because it is also possible to let the absorber shrink, by letting the absorber and the first crotch elastic member shrink integrally, these webs and the absorber of the completed wearing article are allowed to fit to the crotch of the wearer.

Further, according to the method described above, because fastening occurs in the absorber due to a shrinkage force of the second crotch elastic member in the completed wearing article, the absorber is pulled upward when put on the wearer, which further enhances the wearing comfort when put on the wearer.

It is preferable that the first crotch elastic member is joined to the crotch outer sheet so as to leave edges of the front outer web and the back outer web in the width direction on mutually opposing sides as non-attachment regions in the attaching step, and that the absorber is joined to the front outer web and the back outer web in the non-attachment regions alone in the absorber joining step.

According to this method, because the crotch outer sheet is allowed to stretch and shrink independently of the absorber in the region where the first crotch elastic member is attached, it is possible to provide the gusset in the crotch portion of the completed wearing article regardless of the stiffness (stretching and shrinking) of the absorber.

Further, in a case where the elastic member (the second crotch elastic member) is attached also to the absorber, because the absorber is allowed to fit to the crotch of the wearer without influences of the stretching and shrinking of the first crotch elastic member in the completed wearing article, it is possible to achieve satisfactory wearing comfort.

It is preferable that dimensions of the front outer web, the back outer web, and the first crotch elastic member used are set in such a manner that a ratio of a length dimension of the first crotch elastic member in the stretched state and a dimension of a space between edges of the front outer web and the back outer web on sides spaced apart from each other immediately before the folding step is performed is 1:15 to 1:2.

According to this configuration, because a ratio of the length dimension of the first crotch elastic member in a stretched state and a dimension of the space between edges of the front outer web and the back outer web on the sides spaced apart from each other immediately before the folding step is performed is set to 1:15 to 1:2, it is possible to form the completed wearing article into the shape of trunks with good appearance.

In the method of manufacturing a wearing article described above, it is preferable to further include a waist elastic member attaching step of attaching a waist elastic member in a stretched state to the front outer web and the back outer web along a longitudinal direction of the both outer webs at edges on sides spaced apart from each other.

According to this configuration, because the waist opening formed between the front outer web and the back outer web can be tightened by the waist elastic member, it is possible to suppress the slipping down when put on the wearer by letting the waist opening fit tightly to the waist of the wearer.

INDUSTRIAL APPLICABILITY

According to the invention, not only is it possible to reduce a loss of materials in comparison with a conventional wearing article that causes a loss of materials in an amount comparable to the opening areas of the leg openings, but it is also possible to reduce the cost of facilities because the facility needed for the work to cut out the leg openings can be omitted.

The invention claimed is:

1. A method of manufacturing a wearing article having a front portion disposed on an abdomen of a wearer and a back portion disposed on a back of the wearer, characterized by comprising:
   a front outer web transporting step of transporting a strip-shaped front outer web used to form the front portion in such a manner that a longitudinal direction thereof aligns with a pre-set flowing direction;
   a back outer web transporting step of transporting a strip-shaped back outer web used to form the back portion in parallel with the front outer web with a specific interval from the front outer web;
   an outer sheet joining step of disposing a crotch outer sheet so as to bridge between the both outer webs and joining the crotch outer sheet onto the both outer webs;
   an attaching step of attaching a first crotch elastic member in a stretched state to the crotch outer sheet in a direction crossing the flowing direction;
   a maintaining step of maintaining the first crotch elastic member in the stretched state;
   an absorber joining step of disposing an absorber so as to cover the first crotch elastic member and joining the absorber at least to top surfaces of the front outer web and the back outer web while the maintaining step is performed;
   a folding step of placing the front outer web and the back outer web one on top of the other by folding the crotch outer sheet; and
   a cutting step of joining the front outer web and the back outer web along a width direction of the both outer webs at positions on both sides of the crotch outer sheet and cutting the both outer webs for every wearing article.

2. The method of manufacturing a wearing article according to claim 1, wherein:
   a second crotch elastic member in a stretched state is attached to the absorber, and the second crotch elastic member is disposed in such a manner that a longitudinal direction thereof aligns with the direction crossing the flowing direction in the absorber joining step.

3. The method of manufacturing a wearing article according to claim 1, wherein:
   the first crotch elastic member is joined to the crotch outer sheet so as to leave edges of the front outer web and the back outer web in the width direction on mutually opposing sides as non-attachment regions in the attaching step; and
   the absorber is joined to the front outer web and the back outer web in the non-attachment regions alone in the absorber joining step.

4. The method of manufacturing a wearing article according to claim 1, wherein:
   dimensions of the front outer web, the back outer web, and the first crotch elastic member used are set in such a manner that a ratio of a length dimension of the first crotch elastic member in the stretched state and a dimension of a space between edges of the front outer web and the back outer web on sides spaced apart from each other immediately before the folding step is performed is 1:15 to 1:2.

5. The method of manufacturing a wearing article according to claim 1, wherein prior to the front outer web transporting step, the method further comprises:
   transporting a strip shaped web along the flowing direction;
   cutting the strip shaped web to define a cut substantially along the flowing direction; and
   separating the strip shaped web on opposite sides of the cut in directions transverse to the flowing direction to form the front and back outer webs.

6. The method of manufacturing a wearing article according to claim 1, wherein the front and back outer web transporting steps are carried out with the strip shaped front and back outer webs spaced from one another by the specific interval.

* * * * *